(12) United States Patent
Zoth et al.

(10) Patent No.: US 6,231,521 B1
(45) Date of Patent: *May 15, 2001

(54) AUDIOLOGICAL SCREENING METHOD AND APPARATUS

(76) Inventors: Peter Zoth, D81241 Munchen Haidelweg 25A, Munich; Armin Giebel, D82393 Iffeldorf, Haffeistr. 12, Iffeldorf; Franz Fischer, D81241 Munchen Haidelweg 27, Munich, all of (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,224

(22) Filed: Feb. 11, 2000

Related U.S. Application Data

(63) Continuation-in-part of application No. 09/213,780, filed on Dec. 17, 1998, now Pat. No. 6,110,126.

(51) Int. Cl.[7] .......................................... A61B 5/00
(52) U.S. Cl. .......................... 600/559; 128/898; 73/585
(58) Field of Search .................................. 600/552, 559; 128/898; 73/585, 587, 589

(56) References Cited

U.S. PATENT DOCUMENTS

| | | | | |
|---|---|---|---|---|
| 4,688,582 | * | 8/1987 | Heller et al. | 600/559 |
| 5,372,142 | * | 12/1994 | Madsen et al. | 600/552 |
| 5,413,114 | * | 5/1995 | Zurek et al. | 600/559 |
| 5,546,956 | * | 8/1996 | Thornton | 600/559 |
| 5,601,091 | * | 2/1997 | Dolphin | 600/559 |
| 5,651,371 | * | 7/1997 | Keefe | 600/559 |
| 5,664,577 | * | 9/1997 | Lonsbury-Martin et al. | 600/559 |
| 5,738,633 | * | 4/1998 | Christiansen | 600/559 |
| 5,885,225 | * | 3/1999 | Keefe et al. | 600/559 |
| 5,954,669 | * | 9/1999 | Iseberg | 600/559 |

* cited by examiner

*Primary Examiner*—Cary O'Connor
*Assistant Examiner*—Charles Marmor, II
(74) *Attorney, Agent, or Firm*—Marcus G. Theodore

(57) ABSTRACT

An audiological screening and testing method for newborns and infants employing audiological screening via statistical phase analysis of otoacoustic emissions in response to acoustic stimuli.

4 Claims, 7 Drawing Sheets

AUDIOLOGICAL SCREENING METHOD AND APPARATUS

RELATED APPLICATIONS

The application is a continuation-in-part application of the original application entitled "Audiological Screening Method and Apparatus", Ser. No. 09/213,780 filed Dec. 17, 1998, now U.S. Pat. No. 6,110,126.

BACKGROUND OF THE INVENTION

1. Field

This invention relates to audiological screening and testing methods. More particularly, it relates to a phase analysis system method and apparatus employing audiological screening via statistical phase analysis of otoacoustic emissions (OAE's), which are signals that are generated by the hair cells of a functioning inner ear in response to acoustic stimuli as a result of the non-linear properties of the cochlear amplifier.

2. State of the Art

Various audiological screening and testing methods are known. For the hearing testing of infants and small children, measurement systems based on the principle of evoked potentials or otoacoustic emissions via signal averaging and individual evaluation by a tester reviewing various wave pattern hearing responses on a display screen are often employed. Because these types of examinations are expensive, and require skilled evaluators, the results often are dependent upon the subjective skills of the evaluator. To overcome these subjective testing limitations, various signal display and evaluation apparatus, such as Kemp, PCT/GB/00030, published Aug. 7, 1981, entitled "Hearing Faculty Testing Apparatus, were developed. These conventional display methods employ methods of frequency and amplitude analysis of otoacoustic emissions (OAE's) signals generated by the inner ear in response to various tones. The frequency and amplitude of the OAE signals are picked up by a microphone and fed into a wave pattern display for measurement and manual or statistical analysis by an operator, see Zoth, DE 4441127A1 published May 23, 1996. These methods and devices may also employ averaging, where a number of signal intervals following the stimulation ("sweeps") are added synchronously with the stimulus, thus improving the signal-to-noise ratio until the emissions are detectable. These other machines thus require an experienced examiner to make a decision based on a number of objectives and subjective criteria such as the frequency spectrum, typical curve morphology and time distributions of the measured signals. The danger in using a normal averaging procedure is that any waveform can be produced by chance. To guard against this, other commercial systems have added additional features such as correlation of two quasi-simultaneous measurements. While this has proven valuable, the amount of correlation depends on the frequency spectrum of noise and signal, which differs from one measurement to another. As a consequence, a given correlation cannot be used exclusively as the criterion for the presence of emissions.

To measure very small signals in general it is necessary to separate the signal from external noise as well as from artifacts caused by the measurement process. A special case is the detection of a time-domain response of a system that does not have a separate input and output. In this case the stimulus signal is part of the recorded response signal. One of these measurement tasks is the measurement of transient evoked otoacoustic emissions (TEOAE). A short signal is applied to the ear canal and a response is recorded by means of a probe microphone. The recorded signal contains the stimulus as well as the desired emission from the inner ear. In general, the TEOAE-signal is recorded in a region of 4 to 20 ms after the stimulus signal. In certain cases the pure acoustic response of the ear canal and the acoustic coupling assembly can have a decay which is that long. One way to separate this artifact from the desired TEOAE-signal is to take advantage of the non-linear character of OAEs. The TEOAE level is not a linear function of the stimulus level but follows a saturation curve. Pure acoustic responses are linear, which means that the response level is a linear function of the stimulus level. Certain stimulus signals can be used to take advantage of the non-linear character of TEOAEs. This paper describes a special class of stimulus signals that improves the detection accuracy of TEOAE measurements.

Commercial available devices for TEOAE-measurements mostly use a non-linear stimulus of a waveform depicted in FIG. 1. The idea is, to present a impulse or click of a certain amplitude once, then present the same signal with a amplitude factor of $-\frac{1}{3}$ 3 times. If the four response signals are added, the stimulus and linear responses compensate and only non-linear responses, such as TEOAE, remain. These summed frames are usually averaged to gain SNR. FIG. 1 shows commonly used stimulus signal for TEOAE-measurements. The 4 parts of the response are summed which compensates the stimulus along with linear responses of the tested system. The sum is calculated according to $s=s(0 \ldots 1)+s(1 \ldots 2)+s(2 \ldots 3)+s(3 \ldots 4)$ where the x-axis values are normalized time-values.

The example in FIG. 1 uses sample rectangular impulses. Clicks or other short signal forms can also be used. The polarity switch between the high impulse and the three low impulses can also be omitted, or be done in the receiver part of the measurement system. Essentially, this polarity switch is what the echo-screen does. The common property all those nonlinear stimuli have is that the amplitude of the single impulses is selected in a way to compensate the stimulus and linear responses at the receiver. Varying gaps can be inserted between the stimulus parts to minimize the influence of periodic external noise. Signal generation and recording have only to be synchronous.

These state-of-the-art signals described above are designed to compensate linear stimulus artifacts, which do quite well in most cases. However, there are some disadvantages of those signals:

- as the signals depend on saturation effects of the inner ear, the stimulus level that is required is quite high: The lower amplitude clicks must have a level within the saturation region, the higher ones are about 10 dB stronger (factor of 3).
- The speakers that are commonly used have magnetic receivers designed for hearing aids. These magnetic receivers have a strong non-linearity on their own with typical total harmonic distortion (THD) values in the 5% region. This means that the stimulus and decay-artifact suppression does in praxis not work very well. This can cause erratic results as the stimulus artifacts are not separated from TEOAEs.

The invention described below provides an improved otoacoustic emissions testing and screening apparatus and method based on a phase analysis system of an analogue signal to provide a "pass"/"fail" or "pass"/"refer" type of response, which is more suitable for automated evaluation without the need for highly trained evaluators.

SUMMARY OF THE INVENTION

The impact of undetected hearing loss in a child is life long in that it interferes with the normal development of communication skills. Early detection of hearing loss allows early intervention, which can reduce the adverse effects of hearing impairment on speech and language development. Sensitivity and specificity for conventional screening procedures carried out in early childhood have been shown to be low. They do not identify all children with significant hearing loss and result in high referral rates. Conversely, diagnostic procedures such as evoked response audiometry are expensive, time-consuming, and require professional expertise to administer the test and interpret the results.

The present invention employs screening based on otoacoustic emissions and fills the gap between conventional screening procedures and evoked response audiometry. It is the only emission-based screening device, which can reliably be used by testers without professional training. This makes it ideally suited for use by physicians and nurses in a pediatric or general practice setting, by personnel in well-baby nurseries, and even by health visitors in home settings.

The method of the invention for audiological screening of infants and newborns comprises first generating a stimulus with acoustic transmitters in both ear canals of the infant or newborn, and then collecting any transient evoked and distortion product otoacoustic emissions generated by the cochlea in each ear canal in response to the stimulus with microphone means to generate a frequency mixed product electronic signal. The frequency mixed product electronic signal from the microphone means and the stimulus frequencies are then inputted into a computer processor. This mixed product electronic signal is amplified with an input amplifier and computer analyzed with the aid of a frequency analyzer and phase analyzer to separate the frequencies comprising the mixed product electronic signal into separate background noise signal components and otoacoustic emissions signal components. A computer calculated statistical evaluation of the otoacoustic emissions signal components with binomial statistics is then run to determine if the otoacoustic emissions signal responses to each stimulus are or are not statistically significant. These statistical conclusions are then displayed on a computer display.

The apparatus of the invention is a miniaturized hearing screening system based upon the measurement of otoacoustic emissions. It consists of a power source operably associated with two stimulus generators with the appropriate acoustic transmitters. The frequency product generated by the cochlea in response to the generated stimulus is measured with the aid of a microphone. The microphone generates an analogue electronic signal fed to an input amplifier. The frequencies of the mixed products of the electronic signal are analyzed with the aid of a frequency analyzer before employing a phase analyzer. The phase analyzer is generally employed to evaluate the $3^{rd}$ order intermodulation product like (2f1–f2), where f2 is approximately equal to 1.2 times f1. This provides the greatest signal amplitude for statistical evaluation as described more fully below. The statistical result is then shown on a "Pass"/"Fail" or "Pass"/"Refer" display, and/or outputted to a printer or PC.

No expertise is required to use the device properly. It is completely microprocessor controlled, and evaluation is done automatically by means of a strict signal statistical criterion. This criterion reduces the probability for a false negative result to less than 1%. The device works as well in analyzing transiently evoked otoacoustic emissions (TEOAE's) and by analyzing distortion product otoacoustic emissions (DEOAE's) described below.

It is based on the measurement and analysis of otoacoustic emissions (OAE's), which are signals generated by the hair cells of a functioning inner ear in response to acoustic stimuli as a result of the non-linear properties of the cochlear amplifier. These OAE signals are measured and assessed in two essential steps:

Step 1. Separation of the Stimulus From the Signals to be Measured

Various routes are followed for this:

Separation in the time range:
If the stimulus is very short (transient stimulus), the measurement window can be selected such that the passive echo from the auditory canal has already decayed again when tie response is recorded. This guarantees that the acoustic signals measured consist only of stimulus-independent sounds and, where appropriate, the OAE's evoked by the stimulus and not of any portion of the stimulus itself or its echo. The responses picked up by the microphone and measured in this way are designated transient evoked otoacoustic emissions (TEOAE's).

Separation in the frequency range:
If continuous sinusoidal sounds are applied as the stimulus, the sound by the inner ear can be separated from the stimulus by analyzing the outside the sound response generated frequencies of the stimuli. Since intermodulation products of the primary frequencies are generated as a result of the non-linearity of the functioning inner ear, the presence of signals whose frequencies do not match ("clash") with the stimulus signals is a deciding factor in proving the integrity of the inner ear. These signals are termed distortion product otoacoustic emissions (DPOAE's). DPOAE's are generated by stimulation with two tones of different frequency. The intermodulation products generated at the cochlea are measured with a microphone, amplified and analyzed with reference to specific mixed frequencies by means of Fourier transformation. This technique which is already known in the art covers a broad frequency range in conventional devices, but no automated evaluation of the results is known.

Step 2. Proof of the Response

An essential feature in interpreting the acoustic signals measured is the proof that the signal actually originates from the inner ear and is not ambient noise. All systems currently used for such measurements exploit the fact that the responses generated by the stimulus, by contrast with noise, are phase-synchronous with the stimulus. Conventionally, an average technique (stimulus-synchronous averaging) is used to repeatedly amplify the signal to be measured in comparison with the noise until it can be identified by an experienced tester as an emission. A frequently used aid is to define a measurement for the "residual noise" and to compare the averaged signal with the residual noise. If the difference between both signals is large, a stimulus synchronous activity may be assumed.

The present invention is based on a phase analysis system described below which, by contrast with the conventional methods of frequency and amplitude analysis is suitable for automated evaluation.

Objectives of the Invention

There are two essential objectives behind the present method and apparatus for measurement and assessment of otoacoustic emissions:

Screening

For screening, it ought to be possible to discover the inner ear activity in an automated system without the judgement of an expert. Non-parametric signal statistics are necessary for this which, in addition to the result "Emission present" also determines an exact figure for the significance level. This enables the quality of the measurement to be defined exactly in relation to the error rate.

Phase Analysis

Every time period evaluated contains a mixture of various signals of differing frequency, amplitude and phase. These signals can be separated from each other by means of a transformation in the frequency spectrum (Fourier transformation).

A properly functioning cochlea responds to sound by active movements of the outer hair cells. This mechanism serves two purposes: it increases sensitivity for low-level sounds, and it increases the frequency resolution of the ear. While the inner hair cells convert the mechanical elongation of the cochlear membrane into the action potentials in about 30,000 nerve fibers, the outer hair cells amplify and tune the incoming sound. The active movement of the outer hair cells produces and results in mechanical energy being transmitted from the inner ear to the outer ear canal via the ossicle chain and the tympanic membrane. The movement of the tympanic membrane creates sound waves in the ear canal. Thus otoacoustic emissions are a byproduct of the active function of the outer hair cells. While otoacoustic emissions often occur spontaneously, they can also be evoked by a transient acoustic stimulus and measured by means of a miniature microphone, which is placed in the ear canal. The amplitude of evoked emissions is quite large in neonates (sometimes corresponding to a sound pressure level of 30 dB) and decreases continuously during the first years of life.

If the stimulus is very short (transient stimulus), the measurement window can be selected such that the passive echo from the auditory canal has already decayed again when the response is recorded. This guarantees that the acoustic signals measured consist only of stimulus-independent sounds and, where appropriate, the OAE's evoked by the stimulus and not of any portion of the stimulus itself or its echo. The responses measured in this way are designated transient evoked otoacoustic emissions (TEOAE's).

The present device is particularly good in dealing with the following disorders and their transient evoked otoacoustic emissions. Transient evoked otoacoustic emissions are highly sensitive to different types of hearing loss. The presence of TEOAE is associated with healthy, well-functioning cochleae and middle ears, while a hearing loss of 30 dB or more which is cochlear or conductive in nature will result in the absence of TEOAE.

Conductive hearing loss is commonly caused by low eardrum motility subsequent to Eustachian tube dysfunction, middle ear effusion, or malformation of outer and middle ear structures. It results in an attenuation of the transmitted acoustic signals in both directions: stimulus as well as emission conduction. Though emissions may be present, their amplitude is decreased to a degree that they are not detectable. Even a mild conductive loss of 10 to 20 dB (corresponding to a signal attenuation factor 3 to 10) can make emission signals undetectable.

Cochlear dysfunction (Cochlear hearing loss) is highly correlated with an absence of transient evoked otoacoustic emissions. No emissions are produced in an inner ear with a broadband threshold elevation of more than 30 dB. The outer hair cells are affected first in nearly all cochlear hearing losses. Frequency specific losses (i.e. notch audiograms) and mild threshold elevations between 5 and 30 dB correlate with missing emissions in a statistical but not unique way. Presence of transiently evoked emissions indicates that peripheral hearing is sufficient for speech acquisition without intervention. Some rare cases of steep audiograms have been described where emissions could be evoked by a transient stimulus in spite of cochlear dysfunction. However, since this type of hearing loss configuration is difficult to verify exactly within the first year of life, providing amplification is too difficult in most of these cases.

Retrocochlear hearing is due to the mechanism of emission production, and cannot be detected by emission measurements. Fortunately, Retrocochlear impairment is extremely rare in infants. The incidence of Retrocochlear pathology is less than 1% of all non-central hearing disorders.

Screening With Emissions

The method and device acts as a screening tool to prove the presence of emissions on a well-defined level of confidence in order to make them useful as a screening tool. Screening should only result in a "pass" or "refer". "Refer" is not necessarily equivalent to pathology—in fact it seldom is—but should serve as a criterion to undergo an audiologic follow-up procedure. A typical testing and evaluation sequence is to test the newborns on the second or third day for transient evoked otoacoustic emissions (TEOAE). If they pass, the newborns are discharged. If they fail, they are re-tested within 15 days. Again, if they pass, they are discharged, but if they fail, they are re-tested again within the third month. If the fail again, they are then referred to habilitation therapy.

Signal Processing for TEOAE

The method and apparatus employs signal processing in order to detect the emission signals in a noise floor caused by environmental and intrinsic acoustic signals. The present invention uses signal statistics to automatically make the decision as to whether the measured signal be regarded as an emission. Specifically, the invention regards each point of the post-stimulus signal interval separately. Thus statistical limitations caused by the time distribution of the signals can be avoided. The basic principle is the "history" of a single timelocked point during a number of sweeps. In a random signal, its distribution is well defined on the principles of binomial statistics. A statistical test for this single point uses the hypothesis that no time locked signal is present. When this hypothesis can be rejected on a 99% level of confidence, this point can be regarded to be influenced by a stimulus response. The invention can be regarded as a device that measures the signal-to-noise ratio rather than the emission signal only. It calculates statistical distributions for 60 points following the stimulus in a time interval from 6 to 12 ms. A "pass" outcome requires 4 pairs of alternating positive and negative peaks that meet the significance.

Signal Processing for (DPOAE's)

The present invention provides an instrument with phase analysis measuring capability of otoacoustic emissions. An essential feature in the evaluation of distortion products is the fact that the frequencies are known at which an inner ear response is anticipated since these are the intermodulation products of the primary frequencies used. Experience shows that the response with the greatest amplitude occurs at a frequency of $2f_1-f_2$ (third order intermodulation product), if $f_2$ is approximately equal to 1.2 times $f1$.

A typical phase analysis is carried out as follows for this frequency (or other intermodulation products of the primary frequencies used):
1. Signal segments of fixed length are continuously generated for which the phases of the two primary signals each have a constant value.
2. These segments are individually subjected to a Fourier transformation (discrete for the selected frequency or FFT). The amount and phase of the frequency to be analyzed, and thus the corresponding vector in the phase diagram, are determined
3. The statistical null hypothesis states:
   "The phases of the vectors of all signal segments are uniformly distributed over the entire angular range between 0 and 360 degrees."
   This uniform distribution corresponds with a purely coincidental noise without reference to the phases of the primary signal. See FIG. 1.
4. If this null hypothesis can be disproved at a defined significance level it may be assumed, given the appropriate significance level, that there is a phase-synchronous signal and therefore a response from the inner ear at the frequency analyzed. To do this, the vector's coordinate plane is divided into two halves. The significance test is carried out for these two halves on the basis of a binomial analysis: every phase value is checked to see whether it lies in one half or the other of the co-ordinate plane. In the first case the statistical reference value is increased by 1, and in the other case decreased by 1. The sum S of these two cases divided by the square root of the number of individual attempts is firmly correlated with the probability that there is only a uniform distribution. If, for example, the value S=3.08 is obtained, there is a residual probability of p=0.001 that only non-phase-synchronous noise is present in the segments analyzed.
5. Some of the segments analyzed are then used to determine the angle in the phase diagram by means of which the uniform distribution is tested, i.e. by which the co-ordinate plane is divided. For this, the vector sum of the individual frequency vectors is formed with these segments. The phase angle of the sum vector +90 degrees (mod 360 degrees) is the angle of the pitch lines through the co-ordinate origin. See FIG. 2 below. The segments used to calculate the phase angle may not be included in the statistics described in paragraph 4 for reasons connected with the signal statistics. Since the analysis is intended to proceed continuously, however, in order to achieve an automatic termination when the specified significance criterion has been met, the following route is recommended.
6. The signal segments are used alternately for sum formation to define the angle and for testing for uniform distribution. Since, therefore, the defined angle changes after every second segment, the angular values used for testing must remain stored and must be constantly tested for uniform distribution against the reference angle current at the time.
7. The measurement is terminated
   when the significance criterion is met, i.e. if the null hypothesis "No" stimulus synchronous signal present" can be refuted with the previously defined significance level or
   if the repeatedly recalculated reference phase angle does not converge within specified limits, or
   if the significance level for refuting the null hypothesis does not reach a specified value
   after analysis of a specified number of signal segments.
   In the latter two cases (6 and 7), the measurement is terminated with, for example, "Fail" (i.e. no signal from the inner ear could be proved), whereas "Pass", for example, is displayed in the first of the three cases (positive proof of a signal).

Signal Processing for (TEOAE's)

The present invention also provides an instrument with phase analysis measuring capability for transient evoked otoacoustic emissions. With transient evoked otoacoustic emissions, a broad frequency band is emitted. This makes it possible to analyze the phase statistics for any arbitrary frequency. The statistical testing sequence can consequently be the same as that used to detect DPOAE's. A measurement segment is transmitted in which the frequencies to be analyzed are determined.

This can be done as outlined in the following example:

A plurality of intervals is formed in the frequency range (e.g. 500–1000 Hz, 1000–2000 Hz, 2000–4000 Hz). The signal segments to be analyzed are alternately written to two buffer stores A and B. The vector of the sum of A and B is then formed for each frequency in accordance with paragraph 5 above. The vector for the difference between A and B is also calculated as a reference value. The frequencies in each specified interval in which the greatest difference is found between the vector of the buffer sum and that of the buffer difference are analyzed. Thereafter the procedure is exactly the same as that described for the distortion product otoacoustic emissions in paragraphs 6 and 7 above.

If the measurement is to be terminated with, for example, "Pass", the requirement is that at least one value must meet the specified significance criterion for each of the specified frequency intervals.

Test Parameters

The method also employs automatic stimulus control. The stimulus level generated by the stimulus generators is optimized for each ear canal and test run. It should be high enough to obtain a good emission response and low enough to avoid stimulus artifacts. In a calibration run, the stimulus is checked for amplitude as well as time constancy. The measurement will start only if both are acceptable. During measurement, changes in stimulus amplitude are registered and the test is stopped if it deviates from what was measured during calibration. In this case, a "stimulus unstable" message will appear on the display.

It also employs artifact rejection. Artifacts are defined as signal periods, which would lower the signal-to-noise ratio if they were included in the averaging procedure. Conventional devices for OAE measurement require a manual artifact rejection control during measurement. The optimal artifact threshold is not known in advance because the signal-to-noise ratio differs extremely from one individual measurement to another. Because of this, the present method tests at different rejection levels simultaneously. As a result testing time is reduced dramatically in most of the cases, especially with restless infants.

Follow-up Procedures

When the method is employed and the apparatus indicates that the signal-to-noise ratio has not been high enough to prove the presence of emissions on the required level of significance, a "refer" condition results. Because this lack of the required level of significance could be attributable to a number of pathologic as well as non-pathologic factors, follow-up diagnostics should be carried out as soon as possible. A frequent flickering of the red light during the measurement indicates that the measurement background has been very noisy. In this case, it is worthwhile to repeat the measurement. This is especially true when 2 or even 3 pairs of peaks have been detected. This information is generally displayed on the liquid crystal display (LCD) screen. The further follow-up-procedure is shown in the diagram. It should start with the examination of the middle ear status because middle ear dysfunction, which is the most frequent origin of mild to moderate hearing loss in early childhood.

Thus, the method and apparatus provides an efficient, highly reliable screening and referral system to test the hearing of newborn infants, which does not require expert evaluators.

DESCRIPTION OF THE ILLUSTRATED EMBODIMENTS

Figure 1:
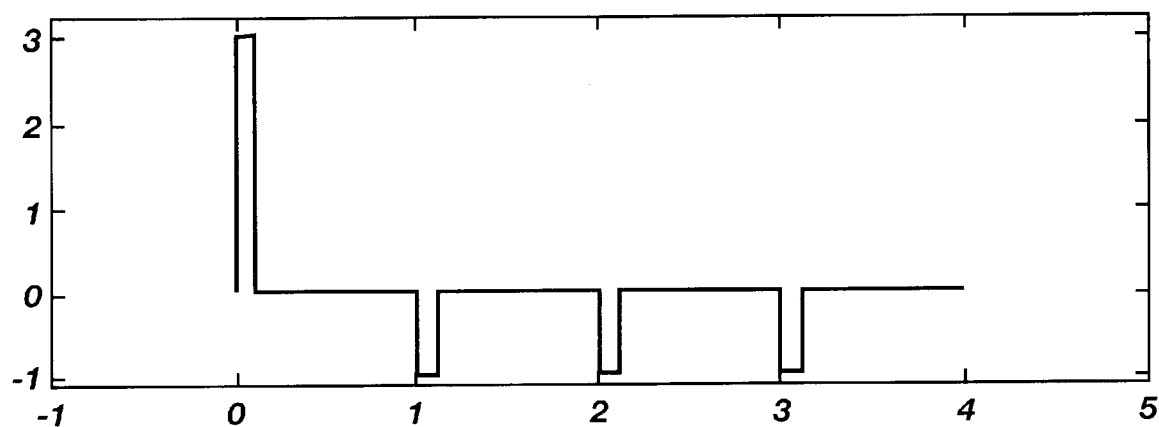
FIG. 1 is a typical non-linear stimulus of a waveform.
Figure 2:
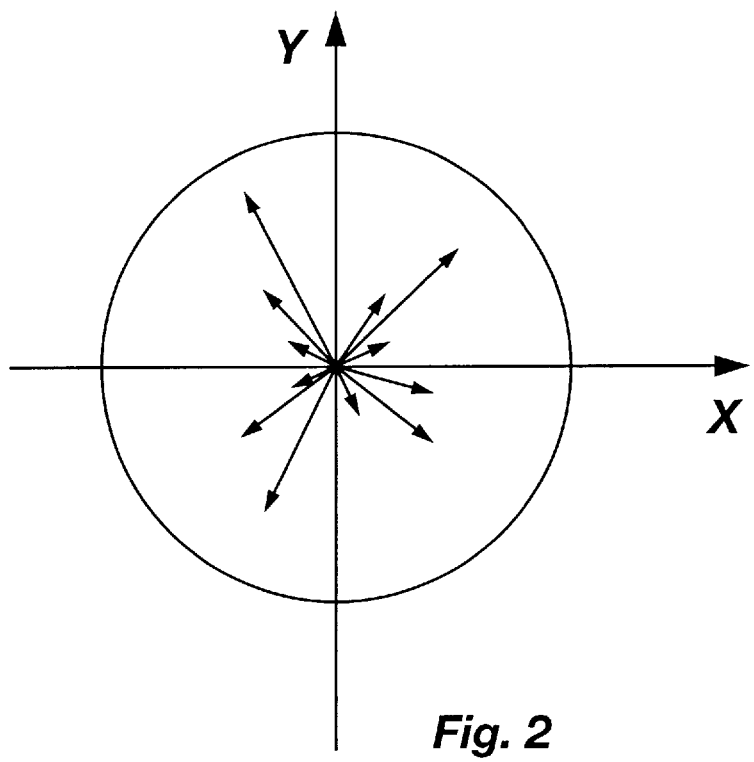
FIG. 2 is a typical Noise pattern showing a uniform distribution in the vector plane.
Figure 3:
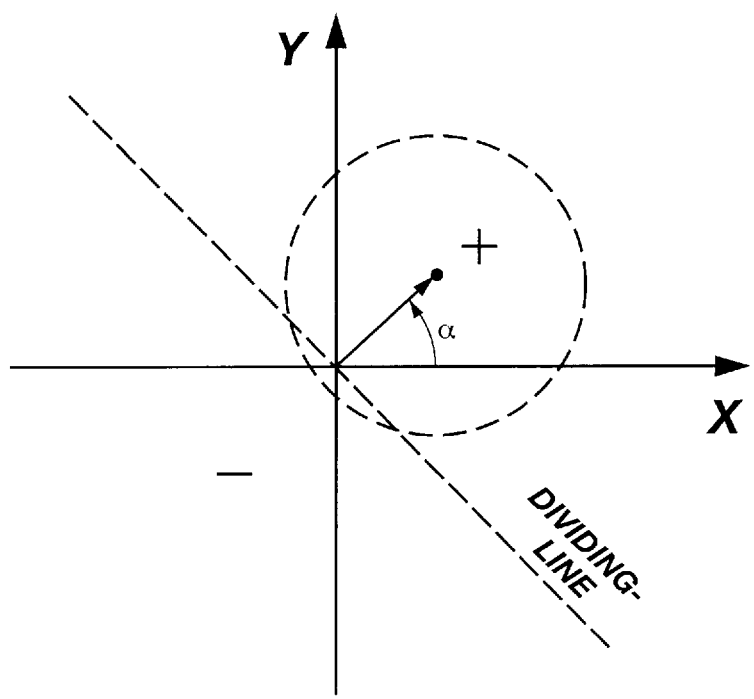
FIG. 3 is a Noise pattern superimposed with constant signal in the vector plane.

The method and apparatus of summary of the invention 10 for audiological screening of infants and newborns described above is incorporated by reference and summarized as follows. It generally comprises first generating a stimulus with acoustic transmitters 12 in both ear canals of the infant or newborn, and then collecting any transient evoked and distortion product otoacoustic emissions generated by the cochlea in each ear canal in response to the stimulus with microphones 13 to generate a frequency mixed product electronic signal. FIG. 2 is a typical Noise pattern showing a uniform distribution in the vector plane. FIG. 3 is a Noise pattern superimposed with constant signal in the vector plane.

Figure 4:
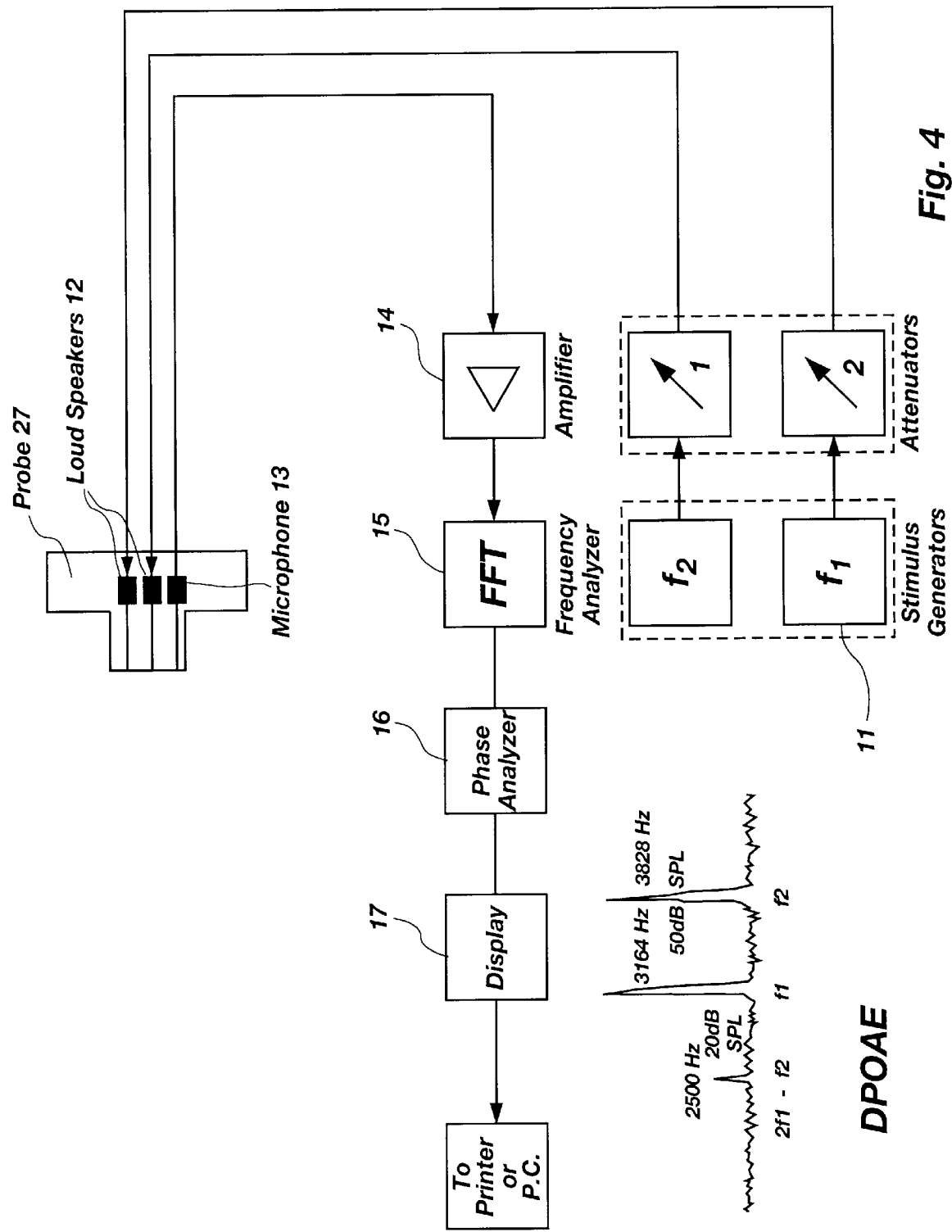
FIG. 4 is a Block diagram of a screening instrument for the measurement, analysis and evaluation of DPOAE's by means of phase analysis.

FIG. 4 shows a block diagram of an instrument of the invention 10 to measure distortion product otoacoustic emissions, which consists of two stimulus generators 11 with the appropriate acoustic transmitters 12. The frequency product generated by the cochlea is measured with the aid of the microphone 13 and fed to an input amplifier 14. The frequencies of the mixed products are analyzed with the aid of a frequency analyzer 15. The phase analyzer 16 contains the means of statistical evaluation referred to above. The result is shown on a display 17 and/or output to a printer or PC or processed further. The method thus employs two stimulus generators 11 with appropriate acoustic transmitters 12 to generate sounds impacting the inner ears of an infant or newborn. The inner ears generate otoacoustic emissions, which are picked up by a microphone 13 and amplified by an amplifier 15 to generate a frequency mixed product electronic signal.

The microphone 13 electronic signals and the stimulus frequencies are then inputted into a computer processor consisting of an amplifier 14, a frequency analyzer 15, and a phase analyzer 16. The mixed product electronic signal is amplified with an input amplifier 14 and analyzed with the aid of a frequency analyzer 15 and phase analyzer 16 to separate the frequencies comprising the mixed product electronic signal into separate background noise signal components and otoacoustic emissions signal components.

Figure 5:
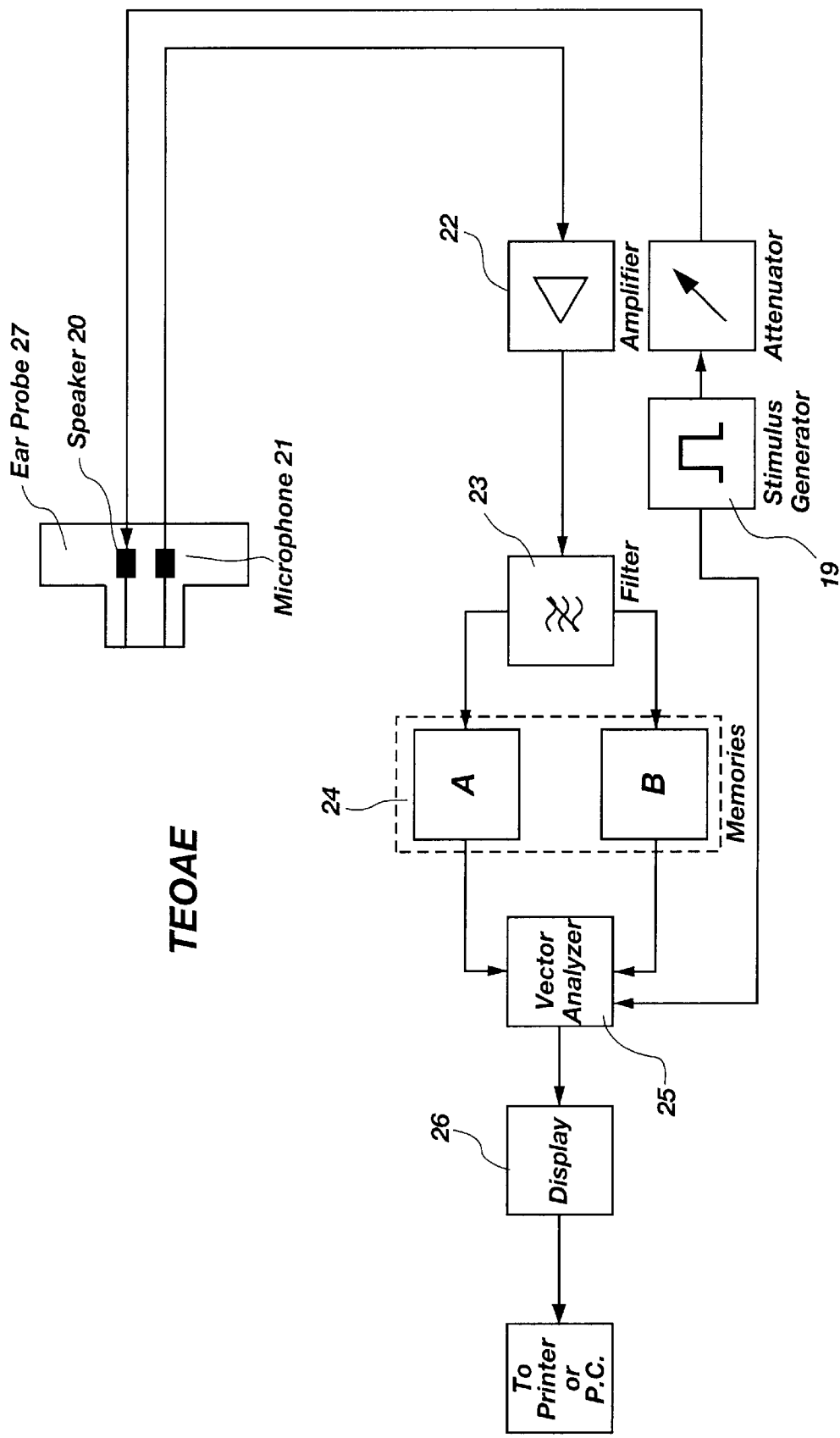
FIG. 5 is a Block diagram of a screening instrument for the measurement, analysis and evaluation of TEOAE's by means of phase analysis.

FIG. 5 shows a block diagram of an instrument of the invention 10 to measure transient evoked otoacoustic emissions. It consists of one stimulus generator 19 with the appropriate acoustic transmitter 20. The frequency mixture generated by the cochlea is measured with the aid of the microphone 21 and fed to an input amplifier 22 and its downstream filter 23 and then stored alternately in different memories 24. Automated evaluation is carried out in the vector analyzer 25 by forming sums and differences. The result is shown on a display 26 and/or output to a printer or PC or processed further. Thus, the frequency analyzer 15 associated with the phase analyzer 16 calculates statistical evaluations of the otoacoustic emissions signal components with binomial statistics to determine if the otoacoustic emissions signal responses to each stimulus are or are not statistically significant. These statistical conclusions are then displayed on a computer display 26.

In summary, the apparatus of the invention 10 is a miniaturized hearing screening system based upon the measurement of transiently evoked otoacoustic emissions. It consists of a power source (not shown) operably associated with two stimulus generators 11 with the appropriate acoustic transmitters 12. The frequency product generated by the cochlea in response to the generated stimulus is measured with the aid of a microphone 13. The microphone 13 generates an analogue electronic signal fed to an input amplifier 14. The frequencies of the mixed products of the electronic signal are analyzed with the aid of a frequency analyzer 15 before employing a phase analyzer 16. The phase analyzer 16 is generally employed to evaluate the $3^{rd}$ order intermodulation product like (2f1−f2), where f2 is approximately equal to 1.2 times f1. This provides the greatest signal amplitude for statistical evaluation as described above. The statistical result is then shown on a "Pass"/"Fail" or "Pass"/"Refer" display 26.

Figure 6:
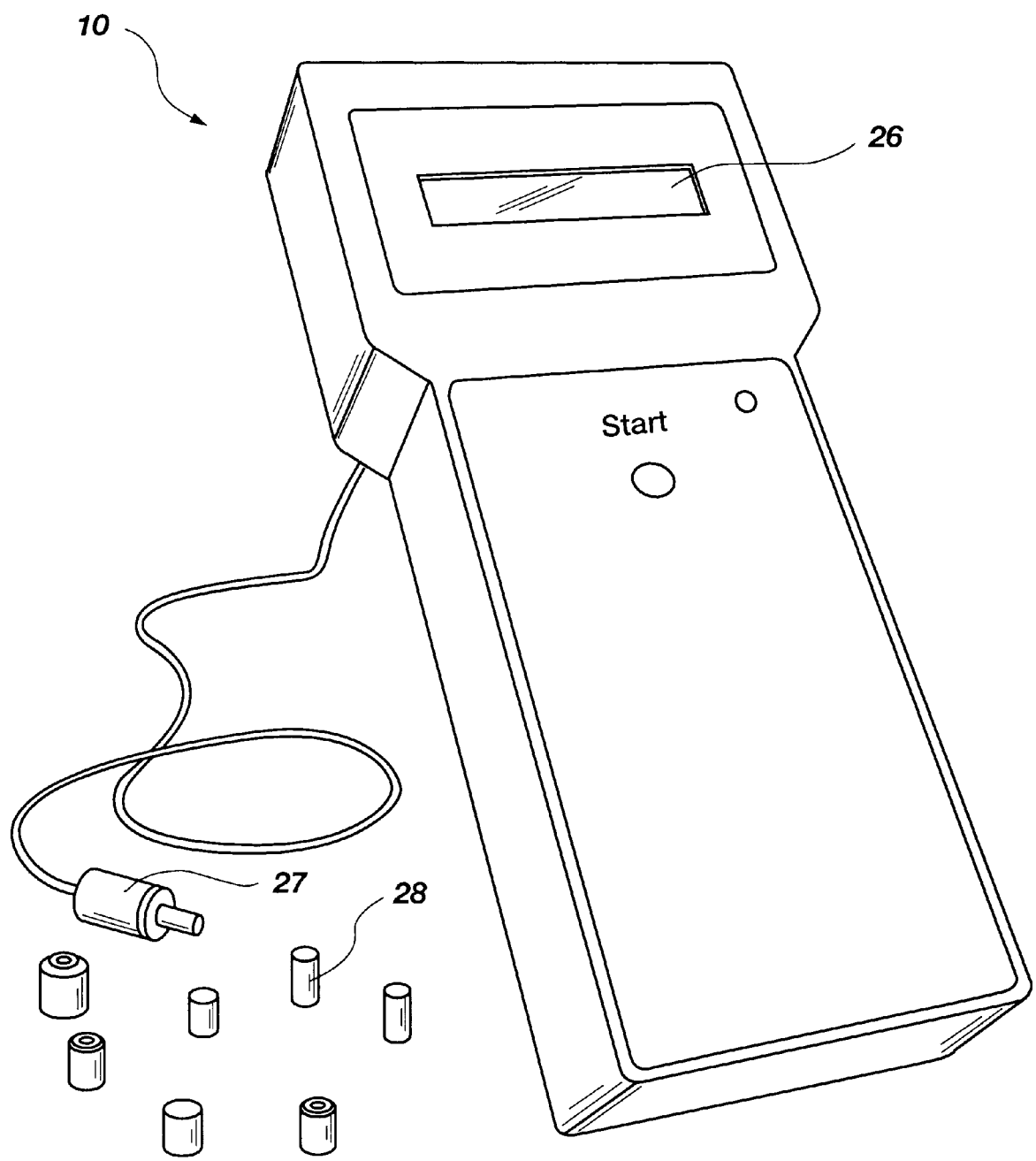
FIG. 6 is a perspective view of a handheld embodiment of the invention.

FIG. 6 illustrates a perspective view of a preferred handheld embodiment of the invention 10 approximately 215× 100×54 mm. and weighs approximately 600 grams. It has at least one combination acoustic transmitter/microphone probe 27 structured to generate stimulus in the ear canals of the infant or newborn and collecting any transient evoked and distortion product otoacoustic emissions generated by the cochlea in response to the stimulus to generate a frequency mixed product electronic signal. The tip of the probe is covered with a disposable soft ear insert 28. The transmitter has a sound stimulus level of 70–85 dB SPL, and a stimulate rate of between 50 to 100 Hz and is microprocessor-controlled. The stimulus type is a non-linear click. The microphone has a band width of 1.4 to 4 kHz with maximum sound pressure limited to 85 dB. The handheld embodiment has a liquid crystal display 26 which indicates artifact rate and stimulus stability. It is battery powered with a 6 volt/1,000 mAh rechargeable battery giving 6 to 7 hours of use.

A preferred embodiment of applicant's method is the One-speaker method. Besides the amplitude-variating stimuli it is possible to use stimuli, which add to zero when summed in groups. These are constructed in different ways. The new method consists of stimuli which add to zero in time-domain structure and/or frequency domain parts—not in amplitude. The principle of this kind of stimuli is illustrated by the examples in FIG. 7 and FIG. 8.

Figure 7:
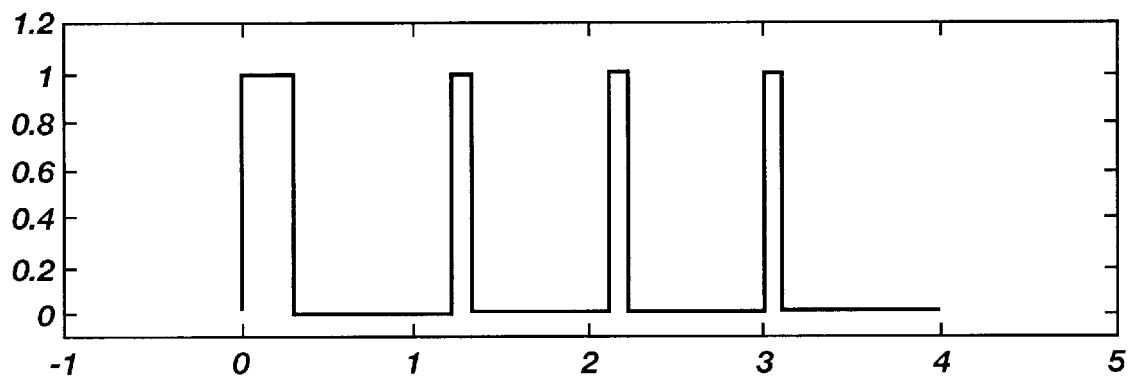
FIG. 7 illustrates two examples of stimulus groups that add to zero when summed.
Figure 7:
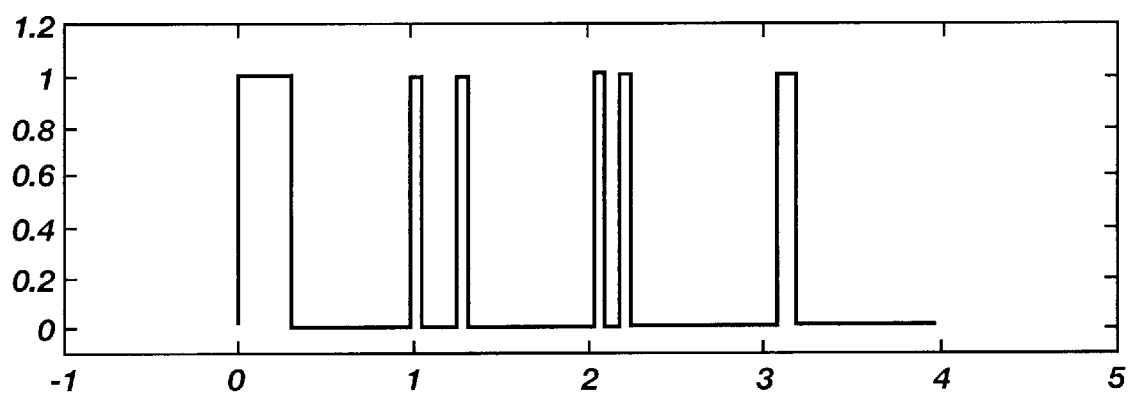

FIG. 7 shows two examples of stimulus groups that add to zero when summed according to s=s(0 . . . 1)-s(1 . . . 2)-s(2 . . . 3)-s(3 . . . 4). The amplitude is not changed to optimize speaker linearity and stimulus level.

Figure 8:
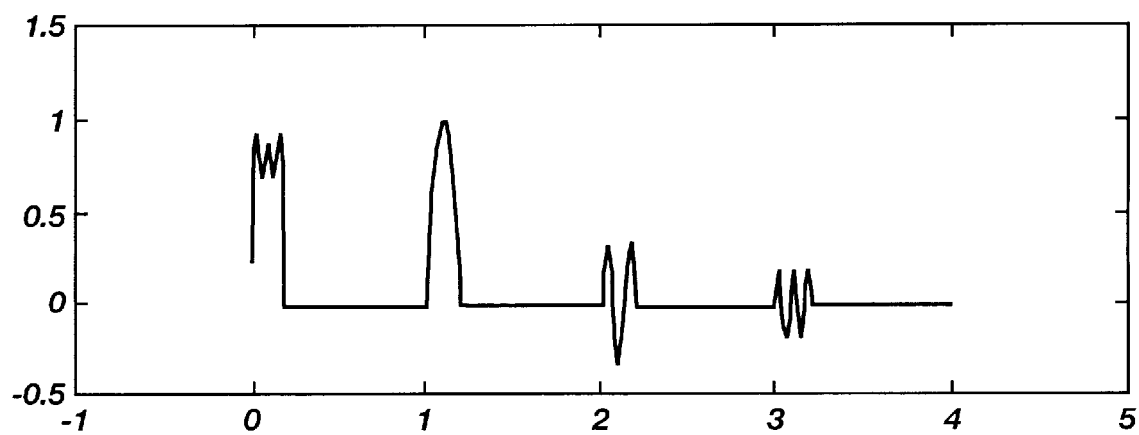
FIG. 8 illustrates an example for a stimulus generated in frequency domain.

FIG. 8 shows an example for a stimulus generated in frequency domain. The group-sum again will be zero with the stimulus parts differing strongly in their spectra.

The illustrated examples use a formula for the group sum of s=s(0 . . . 1)-s(1 . . . 2)-s(2 . . . 3)-s(3 . . . 4), e.g. do a polarity switch on the receiver part. It is of course also possible to invert some of the elements at the sender part instead although the effect will usually not be good. The number of 4 single stimulus elements for a group is also possible, though any number greater then or equal to 3 could be used. The best results are to be expected with numbers from 3 to 5. The main advantages of these type of signals are:

The speaker can be driven with lower maximum levels. For the example drawn in FIG. 2m the voltage is equal for all stimulus elements. This simplifies the stimulus generation part and is very tolerant against non-linearity's in the stimulus generation part including the speaker.

The overall stimulus level can be set lower without sacrificing measuring performance, as experiments have shown.

Another preferred embodiment of applicant's method is the Two-Or-More-Speaker method. This method suppresses non-linear effects of the stimulus generation including the speaker is by using 2 or more speakers with part the stimulus to the speakers used such that each speaker is always driven with the same signal. An example to illustrate this is shown in FIG. 8. Two speakers send the signals named A and B which are then acoustically, and therefore linearly added. The resulting acoustical signal generally looks much the same as signals that are already known. The new idea is to use more then one speaker and separate the stimulus signal in a way that the negative influence of non-linear effects of each signal generation assembly (including the speaker) is minimized. In the example, this is reached by only applying one same waveform to each speaker at varying times.

Figure 9:
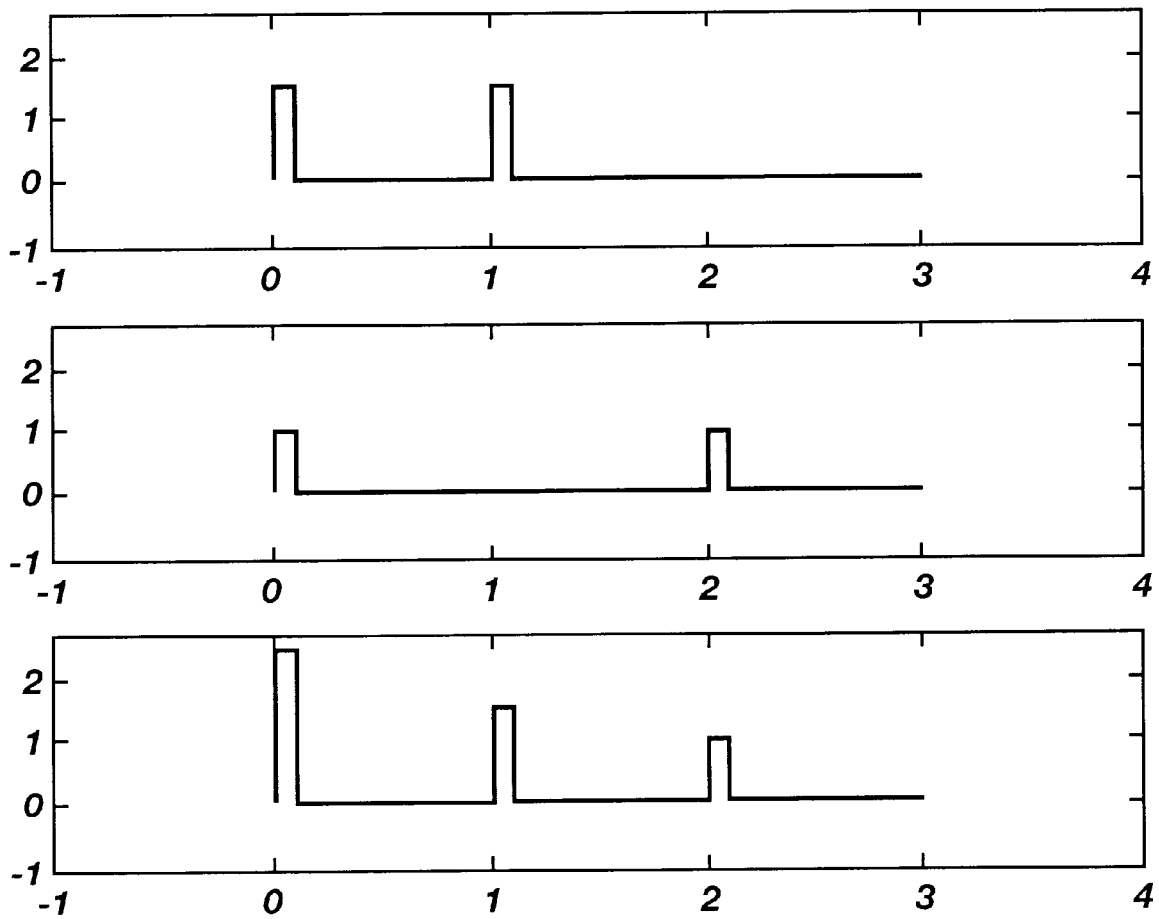
FIG. 9 illustrates an example of generating a stimulus signal by means of two loudspeakers.

FIG. 9 is an example of generating a stimulus signal by means of two loudspeakers. Speakers A and B generate the upper two signals, which are added acoustically and form the lower waveform. The receiver part would have to subtract the response to the two late impulses from the response to the first one.

Thus, signal groups that add or subtract to zero when sequentially recorded and reveal non-linear components of system responses are used for the detection of TEOAEs. Apart from the commonly used signals that consist of groups of impulses or clicks with amplitudes that add or subtract to zero, the claimed signals add or subtract to zero by means of different time-patterns or frequency components. All kind of signals are claimed that do not only use the known amplitude varying method. The main advantages compared to the state of the art are:

the influence of non-linear effects of the signal generation including the speaker(s) can be reduced.

the overall acoustic stimulus level can be reduced without sacrificing measurement time or accuracy.

The preferred method also generates stimulus signals for TEOAE using more then one electro-acoustic converter. In currently used equipment, TEOAE are measured by means of a transient stimulus signal scheme generated by a small loudspeaker. Two speakers are currently used only for detecting distortion-product otoacoustic emissions (DPOAE). The preferred method allows usage of all methods that use stimulus signals for TEOAE measurements to more then one speaker. The main advantage of using the preferred method is to minimize non-linear effects of the speakers.

Although this specification has made reference to the illustrated embodiment, it is not intended to restrict the scope of the appended claims. The claims themselves recite those features deemed essential to the invention.

We claim:

1. A method for audiological screening of infants and newborns comprising:

a. generating one or more stimuli which add or subtract to zero when sequentially recorded with acoustic transmitters in each ear canal of the infant or newborn, b. collecting any transient evoked and distortion product otoacoustic emissions generated by the cochlea in each ear canal in response to the stimulus with microphones for generating a frequency mixed product electronic signal, c. inputting the frequency mixed product electronic signal from the microphones and the stimulus frequencies into a computer processor, d. amplifying the frequency mixed product electronic signal with an input amplifier, e. computer analyzing the frequencies of a measured acoustic signal by means of a frequency and phase analyzer to separate the different frequencies and phases from one another, f. computer statistically evaluating the different acoustic signal components separately by means of binomial statistics to determine whether the measured signal contains stimulus elicited components for each frequency on a defined level of significance, and g. displaying if the oloacoustic signal response is or is not statistically significant on a computer display.

2. A method for audiological screening of infants and newborns according to claim 1, wherein the generated stimuli add or subtract to zero by means of different time-patterns.

3. A method for audiological screening of infants and newborns according to claim 1, wherein the generated stimuli add or subtract to zero by means of different frequency components.

4. A method for audiological screening of infants and newborns according to claim 1, wherein more than one electro-acoustic converter is used to generate stimuli.

* * * * *